United States Patent
Kanigan

(10) Patent No.: US 9,763,693 B2
(45) Date of Patent: Sep. 19, 2017

(54) SAFETY SCALPEL

(71) Applicant: SCALPEL INNOVATION, INC., Burnaby (CA)

(72) Inventor: Ryan Kanigan, Burnaby (CA)

(73) Assignee: Scalpel Innovation, Inc., Burnaby, BC (CA)

( * ) Notice: Subject to any disclaimer, the term of this patent is extended or adjusted under 35 U.S.C. 154(b) by 19 days.

(21) Appl. No.: 14/636,440

(22) Filed: Mar. 3, 2015

(65) Prior Publication Data

US 2015/0164539 A1 Jun. 18, 2015

Related U.S. Application Data

(63) Continuation-in-part of application No. 14/397,172, filed as application No. PCT/CA2013/000312 on Apr. 2, 2013.

(60) Provisional application No. 61/638,559, filed on Apr. 26, 2012.

(51) Int. Cl.
*A61B 17/3209* (2006.01)
*A61B 17/3213* (2006.01)
*A61B 17/3211* (2006.01)

(52) U.S. Cl.
CPC . *A61B 17/3213* (2013.01); *A61B 2017/32113* (2013.01)

(58) Field of Classification Search
CPC .................. A61B 17/3213; A61B 2017/32113
See application file for complete search history.

(56) References Cited

U.S. PATENT DOCUMENTS

| | | | | |
|---|---|---|---|---|
| 5,527,329 | A * | 6/1996 | Gharibian | A61B 17/3213 30/151 |
| 5,741,289 | A * | 4/1998 | Jolly et al. | A61B 17/3213 606/172 |
| 5,752,968 | A * | 5/1998 | Jolly et al. | A61B 17/32 30/162 |
| 5,827,309 | A * | 10/1998 | Jolly et al. | A61B 17/32 128/898 |
| 6,626,925 | B2 | 9/2003 | Newman et al. | |
| 6,757,977 | B2 | 7/2004 | Dambal et al. | |
| 7,207,999 | B2 | 4/2007 | Griffin et al. | |
| 7,346,989 | B2 * | 3/2008 | Shi | A61B 17/3213 30/151 |
| 7,485,126 | B2 * | 2/2009 | Adelman et al. | A61B 17/3213 30/155 |
| 7,669,337 | B2 * | 3/2010 | Yi et al. | A61B 17/3213 30/155 |
| 7,857,824 | B2 | 12/2010 | Kiehne | |
| 7,900,362 | B2 * | 3/2011 | Djordjevic et al. | A61B 17/3213 30/162 |
| 8,015,712 | B2 | 9/2011 | Yi et al. | |

(Continued)

*Primary Examiner* — Hwei C Payer
(74) *Attorney, Agent, or Firm* — Gavrilovich, Dodd & Lindsey LLP

(57) ABSTRACT

An ergonomically balanced safety scalpel that includes a pair of matched handle halves slidingly cooperative into a closed position and an open position. When in use, the handle halves are slidingly positioned in the closed position to expose the blade. The handle halves are slidingly repositioned relative to each other into the open position, when the safety scalpel is not in use, to extend one handle half relative to the other handle half whereby the blade is shielded therebetween.

17 Claims, 14 Drawing Sheets

(56) References Cited

U.S. PATENT DOCUMENTS

| | | | |
|---|---|---|---|
| 8,114,103 B2* | 2/2012 | Rasco | A61B 17/3213 30/151 |
| 8,875,405 B2* | 11/2014 | Trees et al. | A61B 17/3211 30/151 |
| 8,959,778 B2* | 2/2015 | Baid | A61B 17/3213 30/151 |
| 2005/0033336 A1 | 2/2005 | Yang | |
| 2006/0095057 A1 | 5/2006 | Yi et al. | |
| 2007/0265651 A1* | 11/2007 | Yi et al. | A61B 17/3213 606/167 |
| 2009/0192538 A1* | 7/2009 | Sandel et al. | A61B 17/3213 606/167 |
| 2010/0036404 A1 | 2/2010 | Yi et al. | |
| 2010/0152755 A1 | 6/2010 | Kehr et al. | |
| 2010/0268258 A1 | 10/2010 | Maxwell | |
| 2012/0036721 A1 | 2/2012 | McHenry | |
| 2012/0245610 A1 | 9/2012 | Hajgato et al. | |
| 2012/0271333 A1 | 10/2012 | Maxwell | |
| 2015/0119913 A1* | 4/2015 | Kanigan | A61B 17/3211 606/167 |
| 2015/0164539 A1* | 6/2015 | Kanigan | A61B 17/3213 606/167 |

* cited by examiner

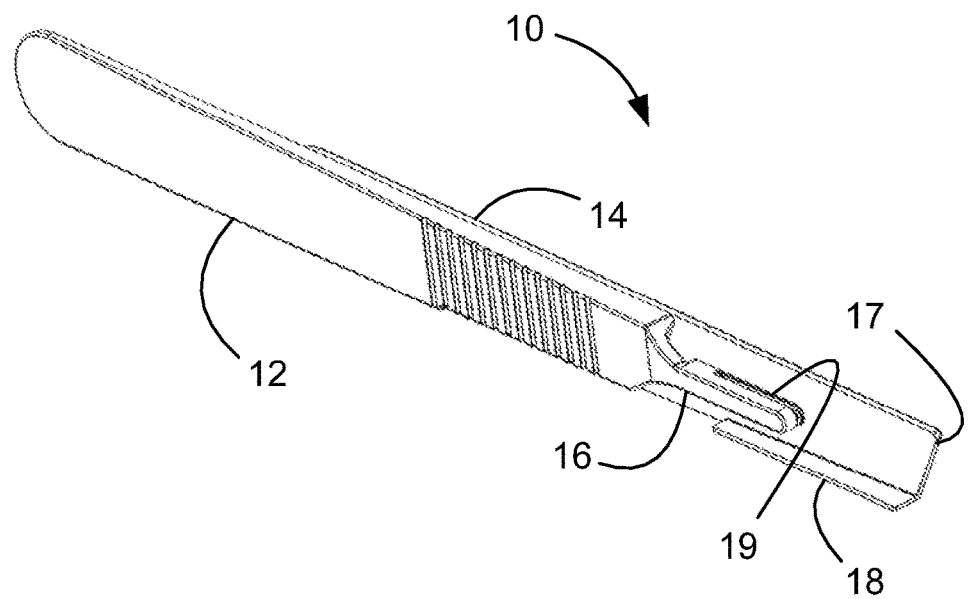
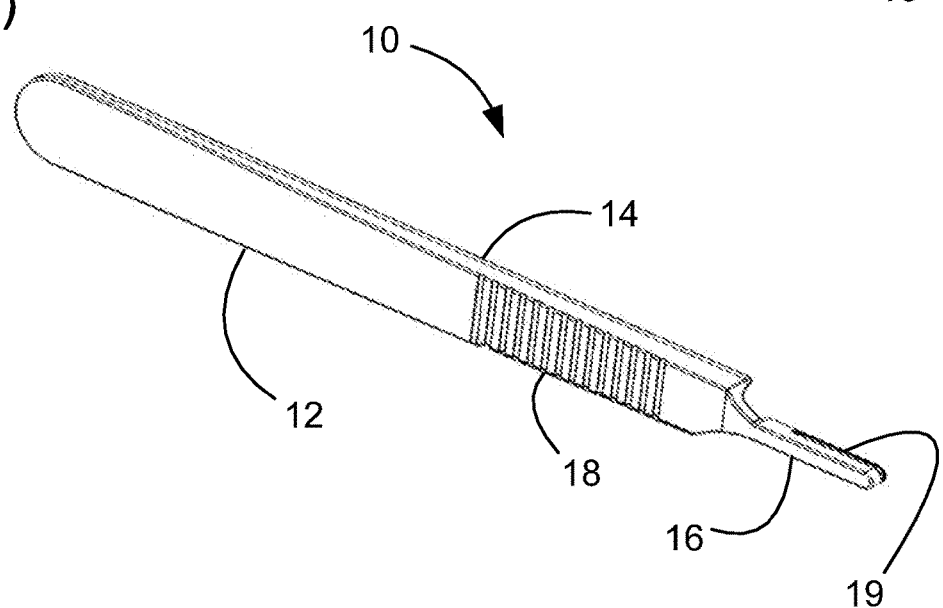
Figure 1A-B (A)
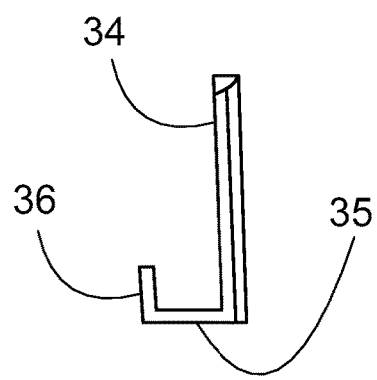
(B)
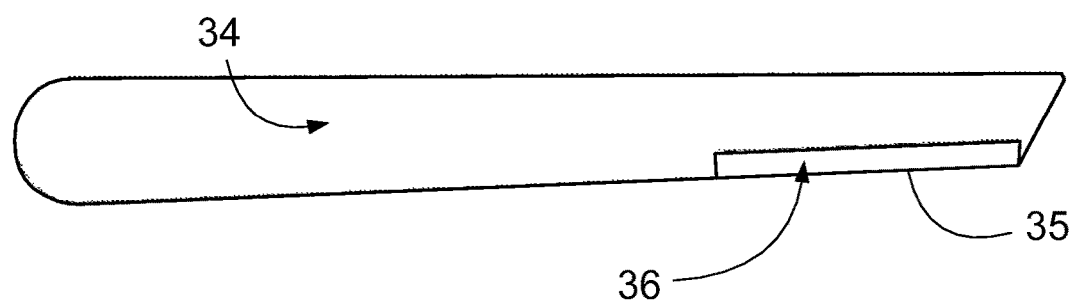
(C)
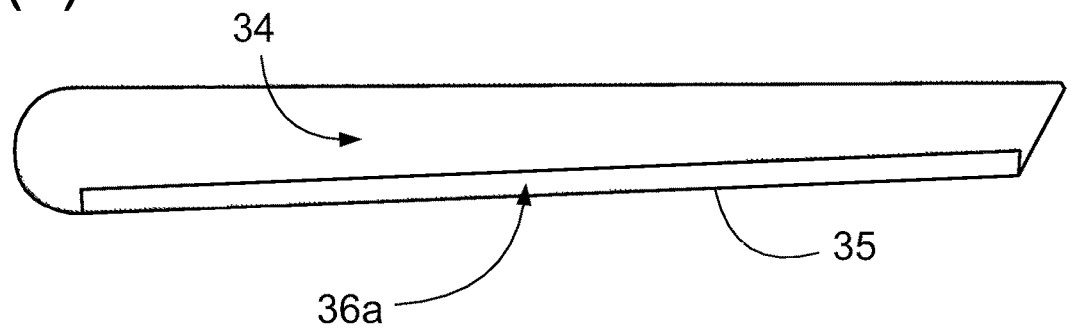
Figure 5A-C

SAFETY SCALPEL

CROSS-REFERENCE TO RELATED APPLICATION

This application is a continuation-in-part of U.S. patent application Ser. No. 14/397,172, filed Apr. 2, 2013, which claims priority from U.S. Provisional Patent Application Ser. No. 61/638,559, filed on Apr. 26, 2012. The contents of all of the aforementioned applications are hereby incorporated herein by reference in their entirety.

FIELD OF THE INVENTION

The present disclosure relates to the field of scalpels and, in particular, to safety scalpels.

BACKGROUND OF THE INVENTION

Scalpels are widely used in surgery the world over. Conventional scalpels used in surgical procedures typically have a cutting blade attached to a metal handle. The blade is attached to the handle via a slot formed in the blade and a corresponding track or lug protruding from the handle. The extremely sharp cutting edges of the blade expose users of scalpels to the risk of accidental cutting or puncturing (or so-called "sharps accidents"). For example, during use in surgery, scalpels can accidentally cut a surgeon's fingers, or the fingers of nurses and other support personnel. Also, the potential for accidents is high when for example the scalpel is being passed back and forth during an operation. If the surgical glove and skin of the surgeon or nurse is accidentally cut via a scalpel blade, there is a risk of transmission of blood borne infectious diseases, and loss of sterility.

To better avoid sharps accidents, various safety scalpels have been developed and made available for use in surgeries, and other medical and non-surgical procedures. Safety scalpels typically have a blade that slides in and out of a cavity in a handle or alternatively a shield that slides over the blade. With proper use of these types of safety scalpels, the sharp edge of the blade is not exposed, except during actual use of the scalpel. However, a problem with these types of safety scalpels is that the cavity in the handle provides an area where blood or other tissue can be deposited. A similar problem arises with safety scalpels that have shields to protect the blades because the shields can also catch and contain tissue, congealed blood, and the like, making it difficult to ensure that the shields are surgically clean to permit the handles with the attached shield to be reused. Cleaning and sterilizing safety scalpels can, therefore, be difficult and/or time consuming, resulting in increased costs and preparatory handling time associated with using safety scalpels.

Irrespective of the above challenges associated with safety scalpels, use of safety scalpels can prevent sharps accidents. However, many surgeons are reluctant to use such safety scalpels for various ergonomic or performance reasons. A common complaint cited against safety scalpels is that they are often of a different size, shape and weight to conventional non-safety scalpels comprising metal handles. For example, to allow reusability the shields must be fairly robust which can result in the shields being of fairly complex manufacture, quite bulky, and quite expensive. As well, typical shield systems often require complex locking and refraction mechanisms that are not user-friendly.

Many surgeons trained with conventional non-safety scalpels object to using safety scalpels because the grip, balance, weight, and/or overall feel of safety scalpel handles are different from conventional scalpel handles. For example, the presence of cavities for blades further creates scalpel handles that are dissimilar to the shapes or weights of conventional scalpel handles. Likewise, the presence of shields for the blades produces different shaped and weighted scalpel handles. The physical and practical differences between conventional safety scalpels and traditional non-safety steel-handled scalpels have reduced the uptake and use of conventional safety scalpels by practitioners of medical sciences or other users.

The different shape of conventional safety scalpels presents further disadvantages. In general, the surgeon's visual sight lines to the blades of conventional safety scalpels are also not as good as with a conventional scalpel, because the front end of the safety scalpel handles are wider, and often also taller, than the front end of conventional scalpel handles. This problem can also limit surgeons' ability to make plunging or puncturing incisions using conventional safety scalpels. As a result, practitioners of medical sciences or other users are reluctant to adopt conventional safety scalpels. There continues to be a need, therefore, for safety scalpels that avoid the drawbacks of conventional safety scalpels and that offer a level of comfort and familiarity to the user.

This background information is provided for the purpose of making known information believed by the applicant to be of possible relevance to the present invention. No admission is necessarily intended, nor should be construed, that any of the preceding information constitutes prior art against the present invention.

SUMMARY OF THE INVENTION

Disclosed herein are exemplary embodiments pertaining to a safety scalpel. An exemplary embodiment of the present disclosure relates to an ergonomically balanced safety scalpel. The ergonomically balanced safety scalpel comprises a pair of matched handle halves wherein a first handle half of the pair is provided with a blade receptacle for engaging therewith a blade; said pair of matched handle halves slidingly cooperative into: (i) a closed position wherein an engaged blade is exposed and extends outside of the pair of matched handle halves, and (ii) an open position wherein a second handle half of the pair is extended relative to the first handle half to cover the engaged blade between the pair of matched handle halves.

In accordance with another aspect of the disclosure, there is described a safety scalpel. The safety scalpel comprises a pair of matched handle halves wherein a first handle half of the pair is provided with a blade receptacle for engaging therewith a blade, the pair of matched handle halves slidingly cooperative into: (i) a closed position wherein an engaged blade is exposed and extends outside of the pair of matched handle halves, and (ii) an open position wherein a second handle half of the pair is extended relative to the first handle half to cover the engaged blade between the pair of matched handle halves; a guide channel extending along the length of one of the pair of handle halves along which the other handle half of the pair slidingly travels; a boss situated on the other handle half, the boss in sliding engagement within the guide channel to allow sliding translation of the pair of handle halves relative to each other; and a locking mechanism for fixing the handle halves into position along the guide channel.

In accordance with a further aspect of the disclosure, there is described a safety scalpel comprising a pair of matched handle halves pivotally connected together wherein a first handle half of the pair is provided with a blade receptacle for engaging therewith a blade, the pair of matched handle halves slidingly cooperative into: (i) a closed position wherein an engaged blade is exposed and extends outside of the pair of matched handle halves, and (ii) an open position wherein a second handle half of the pair is pivotally extended relative to the first handle half to cover the engaged blade between the pair of matched handle halves; a fastener for pivotally connecting the matched handle halves; and a locking mechanism for fixing the handle halves into the open position or closed position.

In accordance with another aspect of the disclosure, there is described a safety scalpel comprising a pair of matched handle halves pivotally connected together wherein a first handle half of the pair is provided with a blade receptacle for engaging therewith a blade, the pair of matched handle halves slidingly cooperative into: (i) a closed position wherein an engaged blade is exposed and extends outside of the pair of matched handle halves, and (ii) an open position wherein a second handle half of the pair is extended relative to the first handle half to cover the engaged blade between the pair of matched handle halves; one or more guide channels extending along the length of one of the pair of handle halves along which the other handle half of the pair slidingly travels; and one or more sliding actuators situated on the other handle half and pivotally engaged with a respective guide channel to allow the handle halves to pivot relative to each other, the one or more sliding actuators further in sliding engagement within the respective guide channel to allow sliding translation of the pair of handle halves relative to each other; wherein the one or more sliding actuators slidingly engage with a corresponding guide channel to allow the handle halves to both slide and pivot relative to each other.

In accordance with a further aspect of the disclosure, there is described a safety scalpel comprising a pair of matched handle halves pivotally connected together wherein a first handle half of the pair is provided with a blade receptacle for engaging therewith a blade, the pair of matched handle halves slidingly cooperative into: (i) a closed position wherein an engaged blade is exposed and extends outside of the pair of matched handle halves, and (ii) an open position wherein a second handle half of the pair is extended relative to the first handle half to cover the engaged blade between the pair of matched handle halves; a pair of guide channels extending from a distal end to a proximal end of the second handle half, the pair of guide channels comprising a pair of flanges extending on opposing sides of the second handle half; a pair of sliding actuators situated at opposing sides of a distal end of the first handle half, each sliding actuator of the pair pivotally engaged with a respective guide channel on the second handle half to allow the handle halves to pivot relative to each other, each of the sliding actuators further in sliding engagement within the respective guide channel on the second handle half to allow sliding translation of the pair of handle halves relative to each other, wherein each sliding actuator slidingly engages with a corresponding guide channel to allow the handle halves to both slide and pivot relative to each other.

BRIEF DESCRIPTION OF THE DRAWINGS

These and other features of the invention will become more apparent in the following detailed description in which reference is made to the appended drawings.

FIG. 1A is a perspective view of an exemplary safety scalpel according to an embodiment of the present disclosure, in an open position;

FIG. 1B is a perspective view of the safety scalpel shown in FIG. 1A in a closed position, according to embodiments of the present disclosure;

FIG. 5A is an end view of a non-blade-bearing handle half, according to embodiments of the present disclosure;

FIG. 5B is a plan view of the non-blade-bearing handle half shown in FIG. 5A, according to embodiments of the present disclosure;

FIG. 5C is a plan view of the non-blade-bearing handle half shown in FIG. 5A, according to further embodiments of the present disclosure;

DETAILED DESCRIPTION OF THE INVENTION

Figure 2:
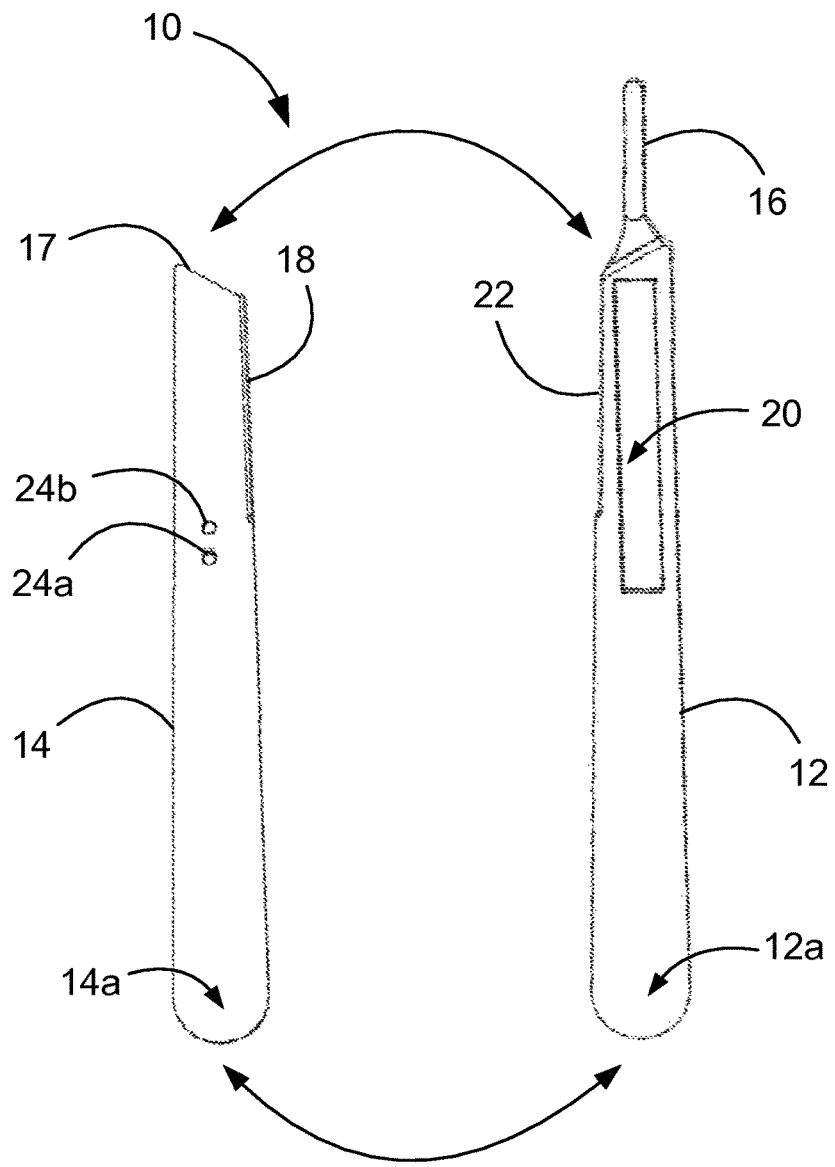
FIG. 2 is a plan view of a safety scalpel according to embodiments of the present disclosure in which the handle halves are separated to show the respective inner faces.

Unless defined otherwise, all technical and scientific terms used herein have the same meaning as commonly understood by one of ordinary skill in the art to which this invention belongs.

As used herein, the term "about" refers to an approximately +/−10% variation from a given value. It is to be understood that such a variation is always included in any given value provided herein, whether or not it is specifically referred to.

Directional terms such as "top", "bottom", "left", "right", "front", and "rear" are used in the following description for the purpose of providing relative reference only, and are not intended to suggest any limitations on how any article is to be positioned during use, or to be mounted in an assembly or relative to an environment.

The exemplary embodiments of the present disclosure relate to ergonomically balanced safety scalpels having a handle that approximates the weight, balance and ergonomic feel of the traditional stainless-steel handled non-safety scalpel. The scalpel handles of the present disclosure comprise a pair of matching handle halves that, when mated together, present outward-facing elongate sides that approximate the size, the shape, the balance, and ergonomic features that approximate conventional non-safety scalpel features.

The handle half itself operates as the protective cover for the blade when the matching handle halves are cooperatively engaged. In this way, protective covering of the blade is achieved without the need for additional parts or complicated shield or cavity systems found with conventional safety scalpels. Further, the simplified design of the embodiments of the present disclosure facilitates cleaning and sterilization allowing the safety scalpel of the present disclosure to be reused.

The handle halves of the safety scalpel of the present disclosure slidingly cooperate with each other to position one handle half over the blade. In some embodiments, the handle halves can be positioned in a "closed position" wherein the blade is exposed, and in an "open position" wherein the blade is covered by one handle half. In some embodiments of the present disclosure, the handle halves can be positioned in a closed and open position as well as intermediate positions therebetween. Positioning of the handle halves between the open and closed positions is accomplished intuitively and can be achieved with one hand.

Embodiments of the safety scalpels of the present disclosure comprise a reusable scalpel handle to permit the significant majority of all disposable scalpel blades to be engaged and concealed. Other embodiments of the safety scalpels of the present disclosure comprise a disposable scalpel handle that can be disposed after each use. Such disposable embodiments comprise, for example, a disposable plastic scalpel handle to which the blade may be permanently fixed by welding or bonding.

Referring now in detail to the figures (FIGS. 1A and 1B), wherein like reference numerals represent like parts throughout the several views, an exemplary embodiment of the safety scalpel 10 of the present disclosure includes a pair of matched handle halves 12,14 which slidingly cooperate into a "closed position" (FIG. 1B) wherein an engaged blade (not shown) is exposed and extends outside of the pair of matched handle halves, and an "open position" (FIG. 1A) wherein the non-blade-bearing handle half 14 is extended relative to the blade-bearing handle half 12 to cover the engaged blade between the pair of matched handle halves 12,14. In this way, the non-blade-bearing handle half 14 provides a protective shield that covers the blade to protect users from inadvertent injury.

The handle halves 12,14 may be fashioned from, among other materials, a metal suitable for use in medical surgeries and the like such as stainless steel and metal alloys, for example. Also suitable are composite materials and polymers that are high-temperature resistant and approximate the weight and ergonomic feel of metals. Use of these materials permit sterilization of the safety scalpels of the present disclosure using both steam and chemical sterilization techniques, thereby protecting patients while allowing the safety scalpel to be reused. Embodiments of the present disclosure include safety scalpels comprising materials that are compatible with cleaning and sterilization protocol and that approximate the weight and ergonomic feel of conventional scalpels. Disposable embodiments of the safety scalpel of the present disclosure may comprise similar materials that approximate the weight and ergonomic feel of conventional non-safety scalpels, however, that are further appropriate for disposable use. Such materials may include, for example, disposable plastics and the like.

Figure 3:
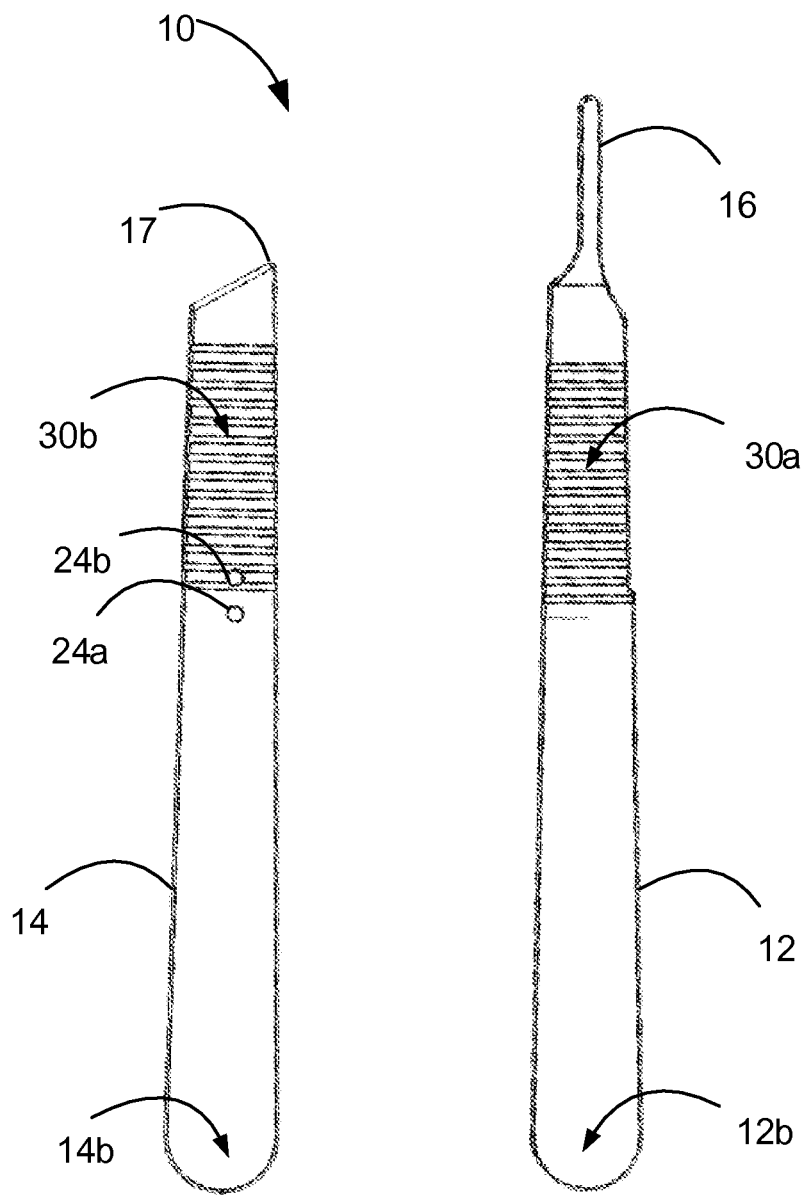
FIG. 3 is a plan view of a safety scalpel according to embodiments of the present disclosure in which the handle halves are separated to show the respective outer faces.

FIGS. 2 and 3 further illustrate the pair of handle halves 12,14 according to embodiments of the present disclosure. Referring to FIG. 3, there is shown the blade-bearing handle half 12 and the non-blade-bearing handle half 14 of the pair of matched handle halves 12,14 separated and laid open on their respective inner faces. Blade-bearing handle half 12 of the safety scalpel 10 has a blade receptacle 16 at one end. The blade receptacle 16 has a blade slot 19 for receiving and engaging a blade (not shown) such that the blade will remain secured to the blade-bearing handle half 12 of the safety scalpel 10. The blade receptacle 16 and the blade slot 19 are of conventional technology and design. In the exemplary embodiment, the blade is pressed onto the blade receptacle 16 and secured in place. In reusable embodiments, the blade is a disposable blade that can be replaced after each use. In other embodiments, for example disposable embodiments, the safety scalpel may be provided with the blade permanently fixed to the blade receptacle 16 and the entire safety scalpel discarded after each use.

As shown by the exemplary embodiment, the outer face 12b of the blade-bearing handle half 12 and the outer face 14b of the non-blade-bearing handle half 14 each have a respective friction surface 30a,30b (together, friction surface 30a and friction surface 30b are referred to as the "friction surfaces 30"). The friction surfaces 30 may be formed by a pattern of dots, dimples, ridges, recesses, or knurled areas. The friction surfaces 30 provide a slip resistant gripping surface for the practitioners of medical sciences or other users near the distal end of the safety scalpel 10, as can be found with conventional scalpels. The friction surfaces 30 assist practitioners of medical sciences or other users to grip the safety scalpel 10 in the hand and thereby maintain good contact with the safety scalpel 10 of the exemplary embodiment. Accordingly, when in use, the safety scalpel 10 is of a similar size, shape and feel as a conventional non-safety scalpel handle and is capable of substantially matching the performance of a conventional non-safety scalpel, for example in terms of visibility of the blade, cutting angles, cutting depth, and clearance around the blade. These features facilitate the adoption and use of the safety scalpels of the exemplary embodiments by practitioners of medical sciences or other users who are reluctant to move away from conventional non-safety scalpels.

Referring now to FIG. 2, the inner faces 12a,14a of the exemplary embodiment are shown wherein the handle halves 12,14 have been separated and laid open on their respective outer faces. As is shown by the directional arrow, the inner faces 12a and 14a are brought together to form the safety scalpel 10 of the present disclosure.

Operation

As shown in FIGS. 1A and 1B, the handle halves 12,14 together form the safety scalpel 10 of the present disclosure. In operation, the handle halves 12,14 slidingly cooperate such that the handle halves 12,14 are slidable relative to each other between an "open position" (FIG. 1A) and a "closed position" (FIG. 1B). In some embodiments, the safety scalpel 10 can also be positioned in various intermediate positions between the "open position" and the "closed position".

In the "open position" (FIG. 1A), the handle halves 12,14 are slidingly translated relative to each other until the distal end 17 of the non-blade-bearing handle half 14 extends to at least the same length as the blade receptacle 16 on the blade-bearing handle half 12 such that the non-blade-bearing handle half 14 shields the blade receptacle 16 and engaged blade (not shown). In this "open position", the non-blade-bearing handle half 14 shields the blade and protects against inadvertent contact with the blade. It will be apparent to those skilled in the art that differing blade lengths and sizes can be shielded by adjusting the relative position of the handle halves 12,14.

To transition the safety scalpel 10 to the "closed position" (FIG. 1B) for use, the handle halves 12,14 are slidingly translated relative to each other to retract the non-blade-bearing handle half 14 such that its distal end 17 does not project or extend beyond the blade receptacle 16 and blade. In this way, the blade receptacle 16 and blade are exposed for use. In the embodiment shown in FIG. 1B, the non-blade-bearing handle half 14 is retracted until the handle ends of the handle halves 12,14 align to form an integrated handle having a conventional scalpel shape. Embodiments of the safety scalpel 10 in the "closed position" have the size, shape and weight of a conventional non-safety scalpel that practitioners of medical sciences or other users will be accustomed to. The exemplary embodiment therefore provides a safety scalpel that is convertible into a working scalpel that is similar to conventional scalpel shapes. In this way, there is a higher likelihood of practitioners of medical sciences or other users of scalpels to adopt the safety scalpel 10 of the present disclosure.

To further approximate the shape and size of a conventional non-safety scalpel, some embodiments of the safety scalpel 10 are tapered such that the end of the safety scalpel 10 that is closest to the blade (the distal end) is broader than the end that is furthest away from the blade (the proximal end). As illustrated in FIG. 1B, the width of the integrated handle halves 12,14 tapers from a broader width at the proximal end to a narrower width at the distal end. In the exemplary embodiment, the rate or degree of taper is consistent. In this way, the safety scalpel 10 is adapted to further approximate the size and shape of conventional metal scalpel handles, for example, in terms of visibility of the blade, cutting angles, cutting depth, and clearance around the blade. As a result, the exemplary safety scalpel 10 provides a solid feel in the surgeon's hand, similar to a conventional metal non-safety scalpel handle.

Guard Flange

In some embodiments, the non-blade-bearing handle half 14 may include additional features in order to provide further protective shielding from the blade engaged on the blade-bearing handle half 12. In the exemplary embodiment shown in FIG. 1A, the non-blade-bearing handle half 14 includes a guard flange portion 18. The guard flange portion 18 projects off from the non-blade-bearing handle half 14 and extends at least beyond the breadth of the blade receptacle 16. In the "open position", when a blade is coupled to the blade receptacle 16, the guard flange portion 18 provides an additional protecting or shielding surface to better shield the blade from an additional angle of contact.

In some embodiments of the present disclosure, the non-blade-bearing handle half 14 of the safety scalpel 10 has a guard flange portion 18 at its distal end 17. The length of the guard flange portion 18 is at least the same length as the blade receptacle 16 (FIG. 5B). In some embodiments, the guard flange portion 18 is about 5% or 10% or 15% or 20% or 50% or 75% longer than the length of the blade receptacle 16. In other embodiments, the guard flange portion 18 extends along the entire length of the non-blade-bearing handle half 14 (FIG. 5C). In further embodiments of the present disclosure, the distal end 17 of the non-blade-bearing handle half 14 may be squared or alternatively inclined.

The guard flange portion 18, as shown in FIG. 1A, may have one linear face 18 that projects approximately perpendicular to the non-blade-bearing handle half 14 of the safety scalpel 10. In further embodiments, the guard flange portion 18 may have more than one face so that it not only projects at an angle approximately perpendicular to the non-blade-bearing handle half 14 but, for example, further bends at a certain angle to further shield the blade receptacle 16 and blade. For example, as shown in FIG. 5A, the guard flange portion may have two faces to provide additional shielding of a blade. The flange portion, according to this embodiment, projects at an angle approximately perpendicular to the non-blade-bearing handle half 34 by base plate 35 which then further bends to form a "J" shape. The bent portion of the base plate 35 projects backward from the front tip of non-blade-bearing handle half 34, as shown in FIG. 5(B), to cover and shield the cutting edge of a blade engaged on the corresponding blade-bearing handle half. In some embodiments, the flange guard is bent at an angle of 30 degrees or 60 degrees or 90 degrees or 120 degrees or 150 degrees from the base plate.

When the safety scalpel 10 is in the "closed position", as shown in FIG. 1B, the guard flange portion 18 rests close to or against the underside of the blade-bearing handle half 12 of the safety scalpel 10. In this way, the guard flange portion 18 is stowed away and the handle halves 12,14 can be aligned into a conventional shape and size for a scalpel without interference.

In order to accommodate the guard flange portion 18, the blade-bearing handle half 12 comprises a recess 22 that corresponds in size to the length of the guard flange portion 18. When the handle halves 12,14 are aligned in the "closed position", recess 22 receives the guard flange portion 18 and in this way allows the guard flange portion 18 to be stowed within the recess 22 during use and does not therefore interfere substantially with the practitioners of medical sciences' or other users' hold on the safety scalpel 10.

Slidingly Cooperative—Guide Channel and Sliding Actuator

The handle halves 12,14 are slidingly cooperative and slide relative to each other between the "open position" and "closed position" as described above. According to some embodiments of the present disclosure, the handle halves 12,14 slidingly cooperate between positions by a guide channel. The guide channel is disposed within one of the pair of handle halves 12,14 and extends along its length. The other handle half of the pair 12,14 is coupled to a sliding actuator that slidingly engages with the guide channel to allow the handle halves 12,14 to slide relative to each other along the length of the guide channel. In this embodiment, it is the length of the guide channel that determines the extent of the relative sliding translation. In order to ensure sufficient shielding of the blade is achieved when the safety scalpel 10 is in the "open position", the guide channel should be at least long enough to permit the non-blade-bearing handle half 14 to slidably extend beyond the length of the corresponding blade-bearing handle half 12 and to cover a blade engaged thereto. Alternatively, the guide channel can extend the length of the corresponding handle half.

Figure 4:
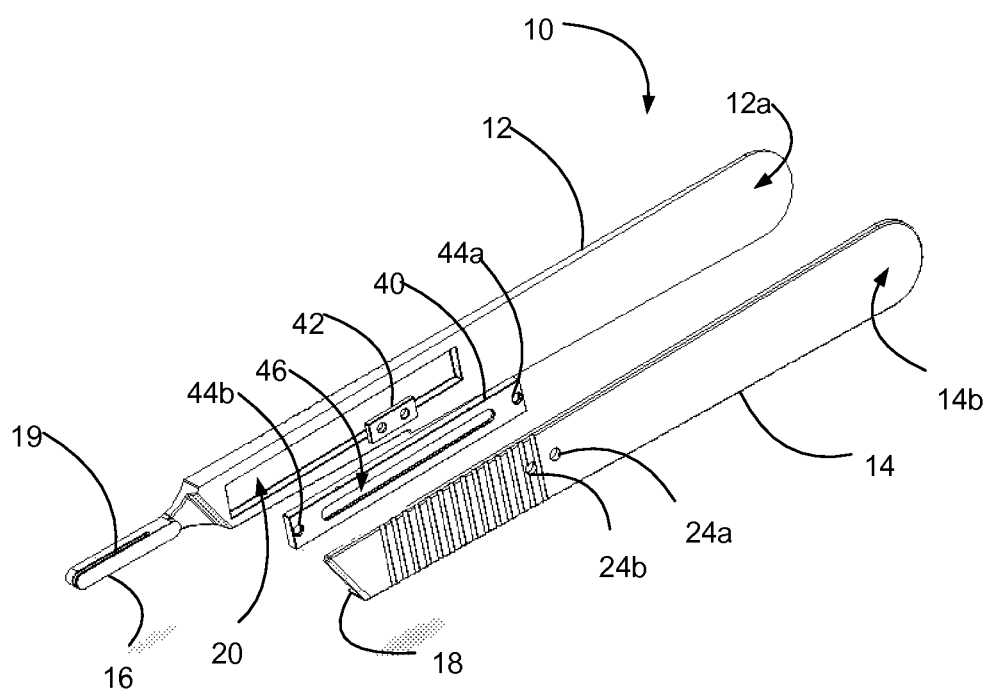
FIG. 4 is an exploded perspective view of an exemplary safety scalpel, according to embodiments of the present disclosure.

In the exemplary embodiment shown in FIGS. 2 and 4, the guide channel 20 is disposed along the length of the inner surface of the blade-bearing handle half 12. The sliding actuator comprises a guide rail 40 that has a groove 46 disposed along substantially the entire longitudinal length of the guide rail 40 and a guide fastener 42 that is sized to slidingly travel within the groove 46 along the length of the guide rail 40. The guide rail 40 is secured within the guide channel 20 by securing means such as bolts or screws through holes 44a and 44b, with the guide fastener 42 situated therebetween. In this way, the guide fastener 42 can move longitudinally within the groove 46 of the guide rail 40 in the guide channel 20.

The guide fastener 42 is coupled to the non-blade-bearing handle half 14 through holes disposed therein 24a, 24b. Securing means such as bolts or screws are passed through the non-blade-bearing handle half 14, through the groove 46 of the guide rail 40, and coupled to the guide fastener 42 through corresponding holes. In the exemplary embodiment, when the non-blade-bearing handle half 14 is coupled to the guide fastener 42, the non-blade-bearing handle half 14 can slidingly move in a longitudinal direction relative to the blade-bearing handle half 12. The pair of matched handle halves 12,14 thereby are slidingly cooperative.

In this embodiment, the extent of the longitudinal movement is determined by the length of the groove 46 in the guide rail 40 and the positioning of the guide fastener 42 on the non-blade-bearing handle half 14. According to embodiments of the present disclosure, the length of the groove 46 and the positioning of the guide fastener 42 on the non-blade-bearing handle half 14 are adapted to permit sliding translation of the non-blade-bearing handle half 14 to extend at least until the distal end of the blade receptacle 16 on the blade-bearing handle half 12 such that the non-blade-bearing handle half 14 shields the blade receptacle 16 and engaged blade.

The handle halves 12,14 of the safety scalpel 10 may be locked in the "open position" or the "closed position" by a locking mechanism. The locking mechanism secures the pair of matched handle halves 12,14 at a selected position relative to each other. For example, practitioners of medical sciences or other users may elect to lock the safety scalpel 10 in the "open position" or the "closed position". Or the safety scalpel 10 may be locked at any position between the "open position" and "closed position" as is required. For example, practitioners of medical sciences or other users may want to expose only a small part of the blade and thereby limit the cutting surface exposed for surgery.

The locking mechanism of the exemplary embodiment may also include an activator element (not shown) to release the locking mechanism. When the activator element is pressed or depressed, the handle halves 12,14 can move relative to each other. When the safety scalpel 10 is placed in the desired position, the locking mechanism can again be used to secure the safety scalpel 10 in that desired position.

The locking mechanism can have several configurations. In some embodiments, a simple friction fit can be employed to set the positioning of the sliding handle halves 12,14. For example, referring to the embodiment shown in FIG. 4, groove 46 in the guide rail 40 and the cooperating guide fastener 42 can be sized to have the desired level of friction required to fix the handle halves 12,14 in the desired position and permit sliding translation upon application of force. In other embodiments, the locking mechanism comprises a protrusion in the guide channel where a pin or boss is forced over a small protrusion to create a locking mechanism.

Figure 6:
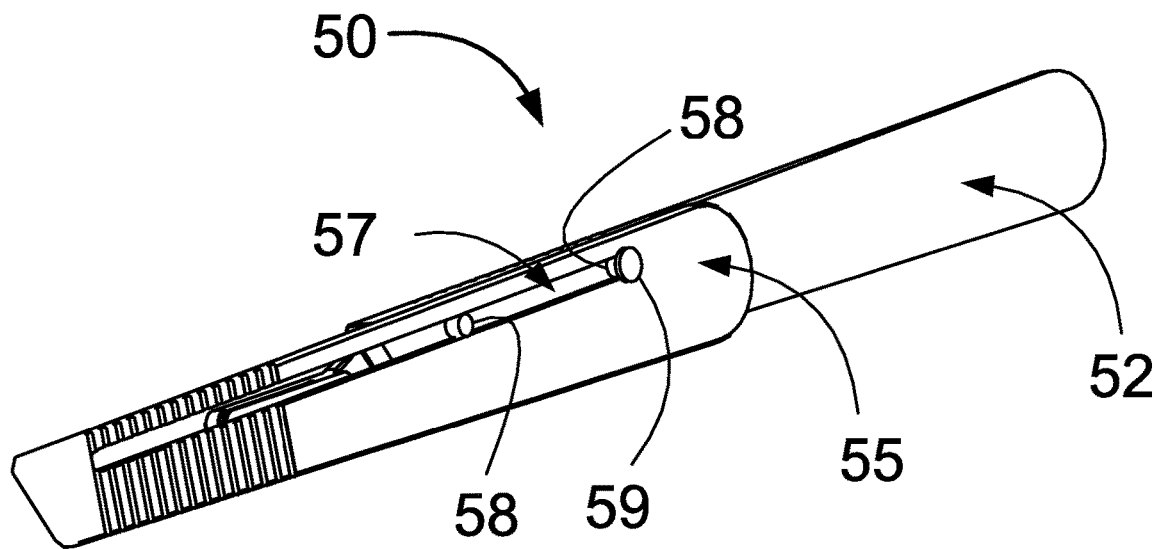
FIG. 6 is a perspective view of a safety scalpel, according to further embodiments of the present disclosure.

Simplified embodiments of the safety scalpel 50 are further described wherein the guide channel 57 is disposed entirely through the length of one of the handle halves 12,14. As shown in FIG. 6, for example, the non-blade-bearing handle half 55 comprises the guide channel 57 through its length. A sliding actuator is coupled to the blade-bearing handle half 52 and comprises one or more bosses 58 that slidingly engage with the guide channel 57 to permit sliding cooperation between the handle halves 12,14. Once in the desired position, the one or more bosses 58 can be configured to threadably engage a locking cap to secure the handle halves 52,55 in an "open position" or a "closed position".

Figure 8A:
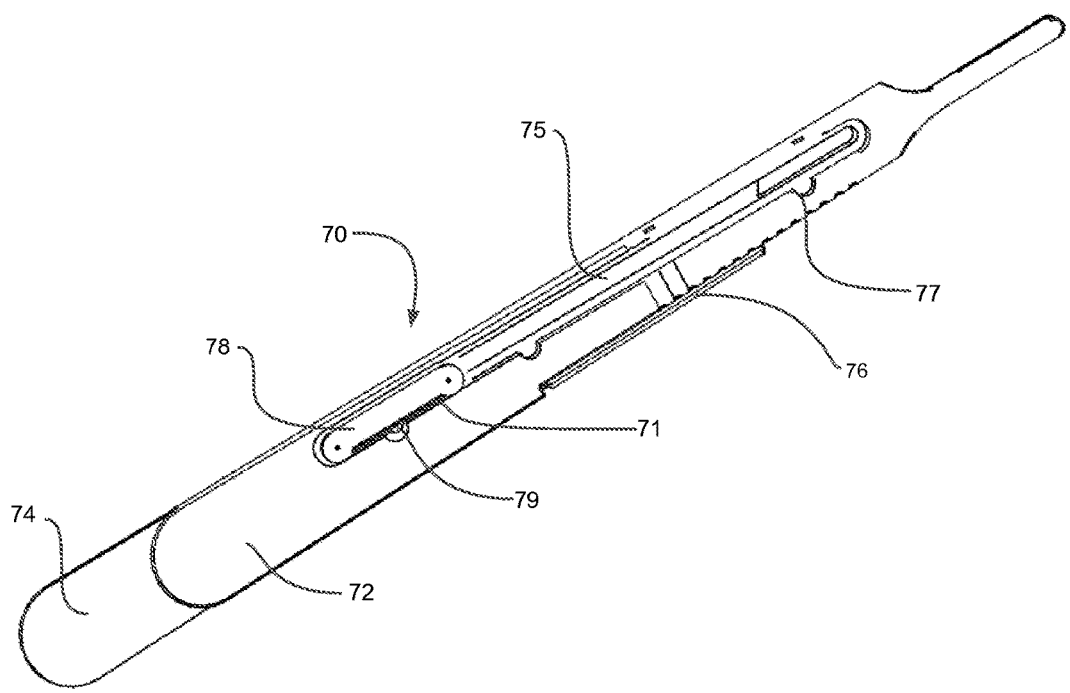
FIGS. 8A, 8B, and 8C are perspective views of a safety scalpel in three respective positions, according to further embodiments of the present disclosure.
Figure 8B:
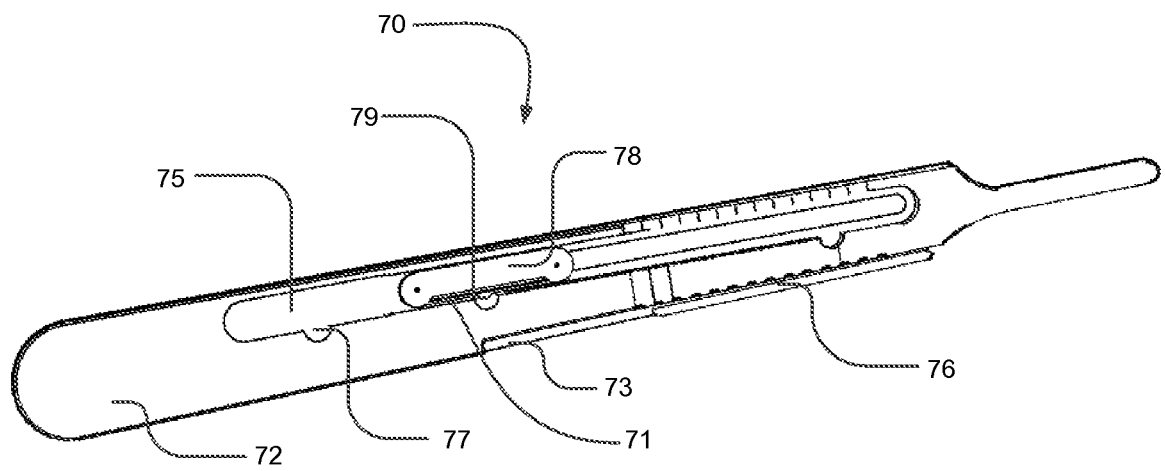
Figure 8C:
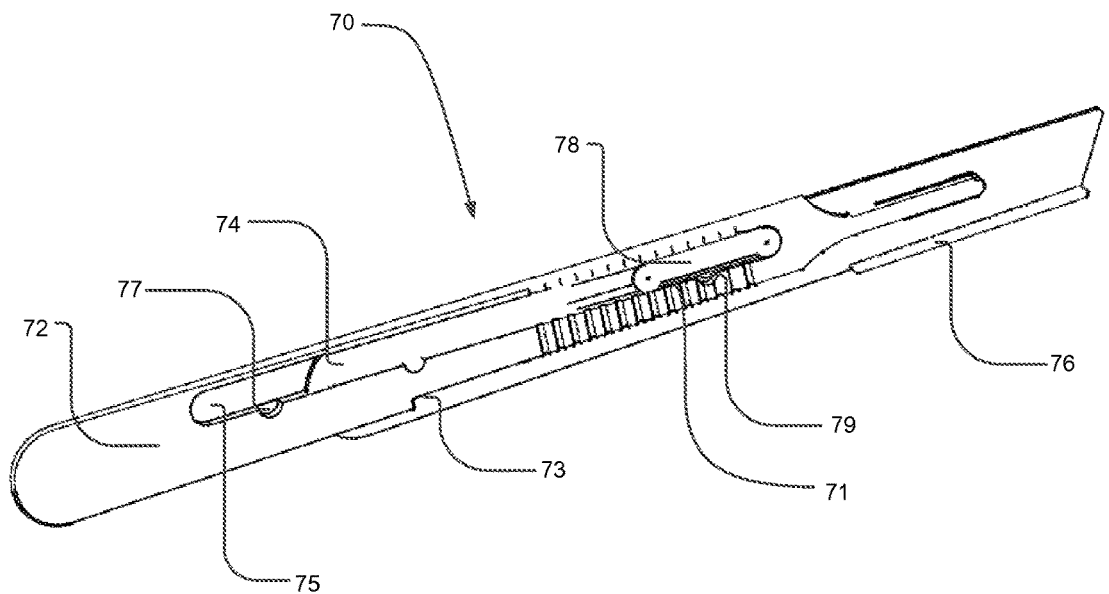

In a further embodiment, the locking mechanism is further simplified. Referring to FIGS. 8A, 8B, 8C, the sliding actuator comprises an elongated boss 78 that slidingly travels along the guide channel 75. The elongated boss 78 has a protuberance 79 that cooperatively engages with one or more correspondingly sized indents 77 situated at fixed positions along the guide channel 75. When engaged, the protuberance 79 and indent 77 effectively lock the handle halves 74,72 into the desired position. In some embodiments, the guide channel 75 comprises two indents 77 positioned to fix the handle halves 74,72 at the "closed position" (FIG. 8A) and "open position" (FIG. 8C). In other embodiments, the guide channel 75 comprises a plurality of indents 77 positioned along the length of the guide channel to fix the handle halves 74,72 in the "closed position" (FIG. 8A) and "open position" (FIG. 8C) and a plurality of positions in between (FIG. 8B). To facilitate ease in locking and unlocking the elongated boss 78, the elongated boss 78 may further comprise a machined-in spring 71 to allow the protuberance 79 to be more easily urged in and out of the corresponding indent 77. In this way, locking and unlocking the safety scalpel 70 and slidably transitioning the safety scalpel 70 between the "open position" and "closed position", can be done intuitively by the user.

Figure 7:
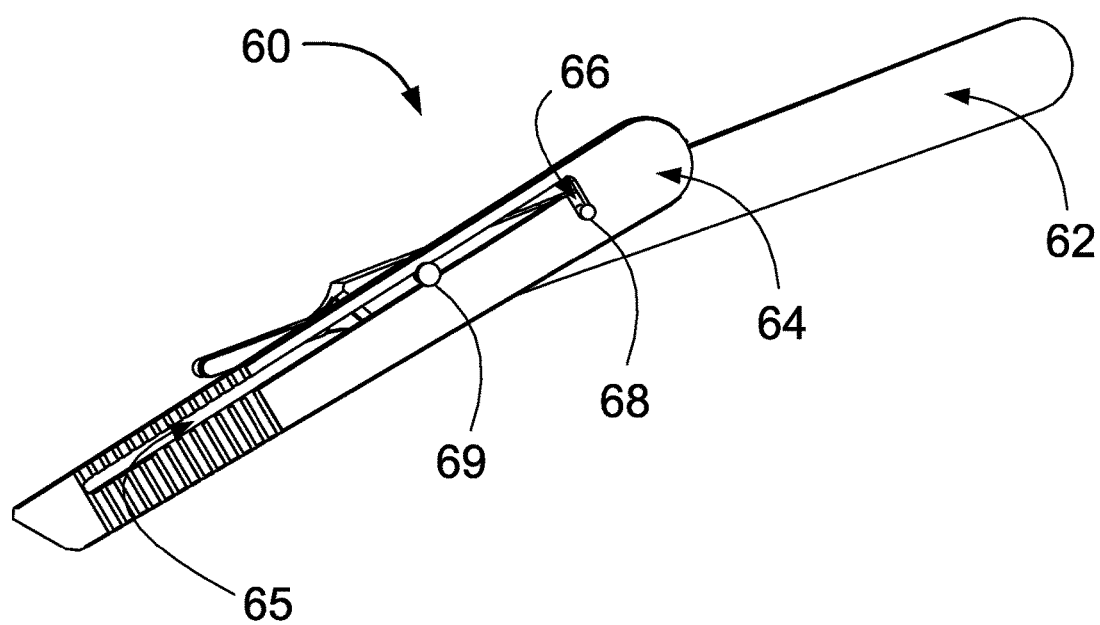
FIG. 7 is a perspective view of a safety scalpel, according to further embodiments of the present disclosure.

Safety scalpels of the present disclosure can be adapted for a variety of types of blades. For example, as shown in FIG. 7 the safety scalpel 60 of the present disclosure can be adapted for use with blades whose designs include bends and/or kinks. These types of blades are used in particular types of surgery, for example, that require a number 3 or a number 12 blade for tasks such as suture cutting or suture removal. This type of safety scalpel may comprise a guide channel 65 that has been adapted to further extend at about a 90° angle to channel 65 at an end section 66. In this way, when in the "open position", boss 68 is engaged in channel portion 66 resulting in further extension of the non-blade-bearing handle half 64 downward relative to the blade-bearing handle half 62, thereby covering and shielding a bent or kinked blade that may be engaged with the blade-bearing handle half 62.

As depicted in the various embodiments described herein, the guide channel and the sliding actuator can be disposed on the non-blade-bearing handle half and the blade-bearing handle half, respectively, and vice-versa.

Slidingly Cooperative—Pivoting Handle Halves

According to further embodiments, the safety scalpel according to embodiments of the present disclosure allow the handle halves to pivot relative to each other.

Figure 9A:
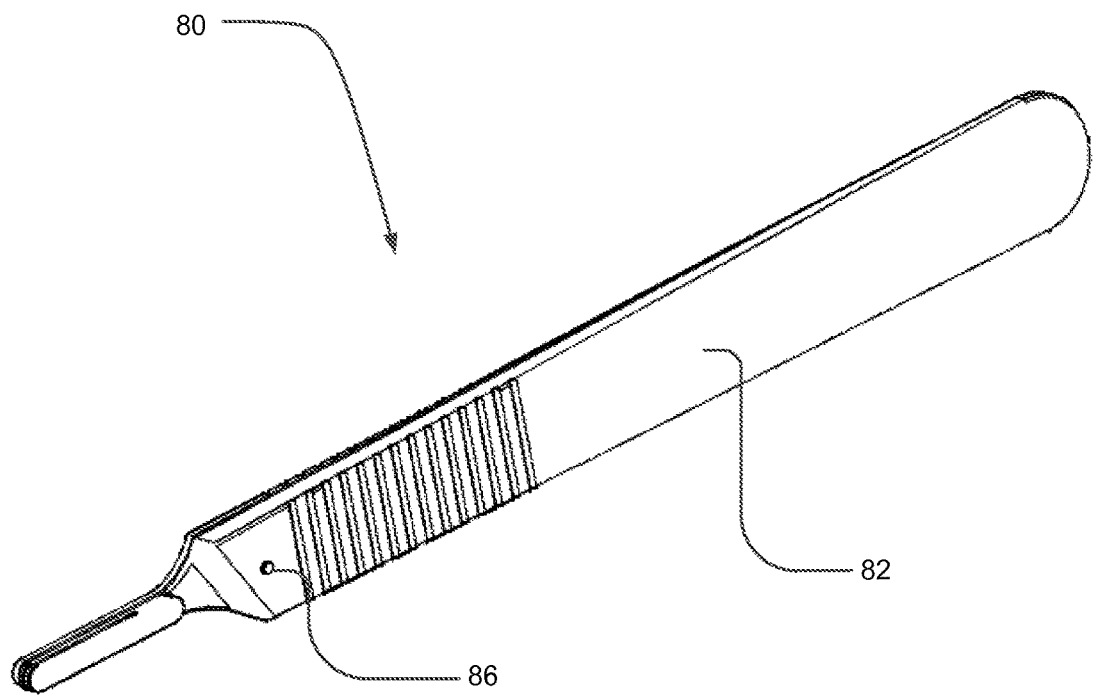
FIGS. 9A and 9B are perspective views of a safety scalpel in a closed and open position respectively, according to embodiments of the present disclosure.
Figure 9B:
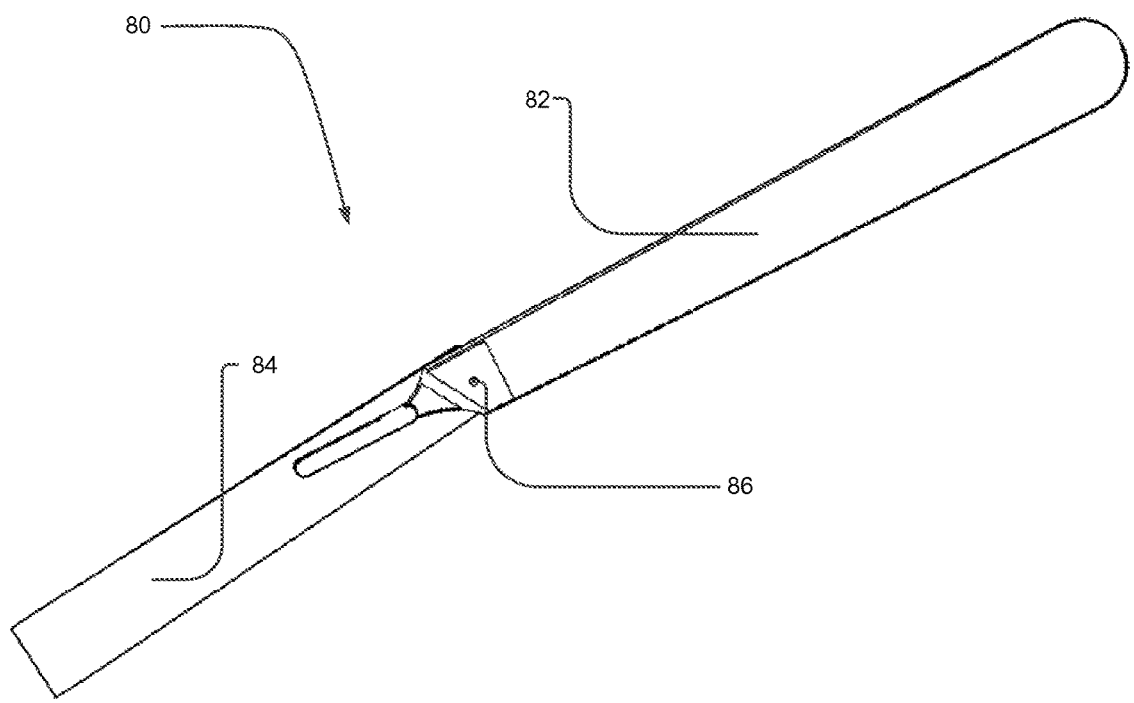

As shown in FIGS. 9A and 9B, the safety scalpel 80 of the present disclosure can be simplified according to certain embodiments. According to such embodiments, the slidingly cooperative handle halves 82,84 transition into an "open position" and a "closed position" by slidingly pivoting relative to each other about a fastener 86 connecting the matched handle halves 82,84. In this embodiment, the non-blade-bearing handle half 84 slidingly pivots about the fastener 86 to flip and extend over the blade-bearing end of the blade-bearing handle half 82. In this way, the safety scalpel 80 is further simplified to a minimum number of parts. The handle halves 82,84 are coupled in friction fit to each other such that application of force is required to slidingly pivot the handle halves 82,84 relative to each other. Once in position, the friction fit permits the handle halves 82,84 to be fixed into position.

Safety scalpels according to certain embodiments of the present disclosure further allow the handle halves to both slide and pivot relative to each other thereby offering a broader range of movement of the cooperating handle halves relative to each other. In this way, the handle halves can not only be transitioned between open and closed positions but can further be pivoted to separate in such a way as to facilitate cleaning of the safety scalpel or to facilitate access to the blade for changing, for example.

Figure 10:
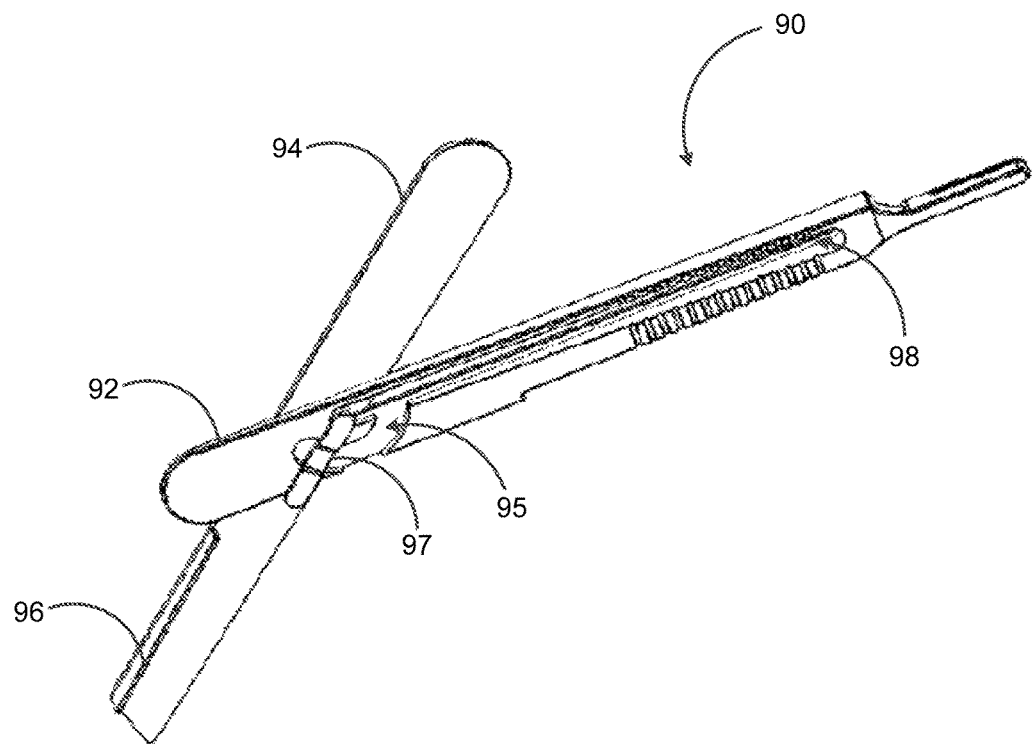
FIG. 10 is a perspective view of a safety scalpel in the open position wherein the non-blade bearing handle half is further pivoted downward from the blade-bearing handle half, according to embodiments of the present disclosure.

According to such embodiments, the safety scalpel can comprise a pair of matched handle halves pivotally connected together to allow pivotal movement of the matching handle halves while allowing the handle halves to slidingly transition between the open and closed positions. Referring to FIG. 10, the matching handle halves 92,94 of the safety scalpel 90 are pivotally connected together by engagement of the sliding actuator 97 on one handle half 94 within the guide channel 98 in the other handle half 92. In this embodiment, the blade-bearing handle half 92 of the pair comprises the guide channel 98 that extends from a distal end to a proximal end of the blade-bearing handle half 92. The non-blade bearing handle half 94 comprises the sliding actuator 97 that cooperatively engages within the guide channel 98 to allow the handle halves 92,94 to slidingly transition between the closed position, wherein an engaged blade is exposed and extends outside of the pair of matched handle halves, and the open position, wherein the non-blade bearing handle half 94 is extended relative to the blade-bearing handle half 92 to cover the engaged blade between the pair of matched handle halves 92,94. The guide channel 98 at the proximal end further comprises a downwardly extending portion 95 which when cooperatively engaged with the sliding actuator 97, situated on the non-blade bearing handle half 94, allows pivotal movement of the distal end of the non-blade bearing handle half 94 in a downward direction away from the blade-bearing handle half 92. In this way, the handle halves pivot relative to each other to allow the pair of handle halves 92,94 to be pivotally separated at the distal end.

According to certain embodiments, the sliding actuator 97 comprises a machined-in spring to facilitate engagement with the downwardly extending portion 95 of the guide channel 98. As described in other embodiments of the present disclosure, the safety scalpel 90 can further include a guard flange 96 as previously described to further cover the engaged blade when in the open position. The guard flange 96 in such embodiments, is sized so as not to interfere with the downward pivotal movement of the non-blade bearing handle half 94. According to such embodiments, the guard flange 96 partially projects from the distal end of the second handle half 94. The blade-bearing handle half 92 has a recess corresponding in size with the guard flange 96 so as to allow the guard flange 96 to be stowed within the recess when the safety scalpel 90 is in the closed position.

Figure 11:
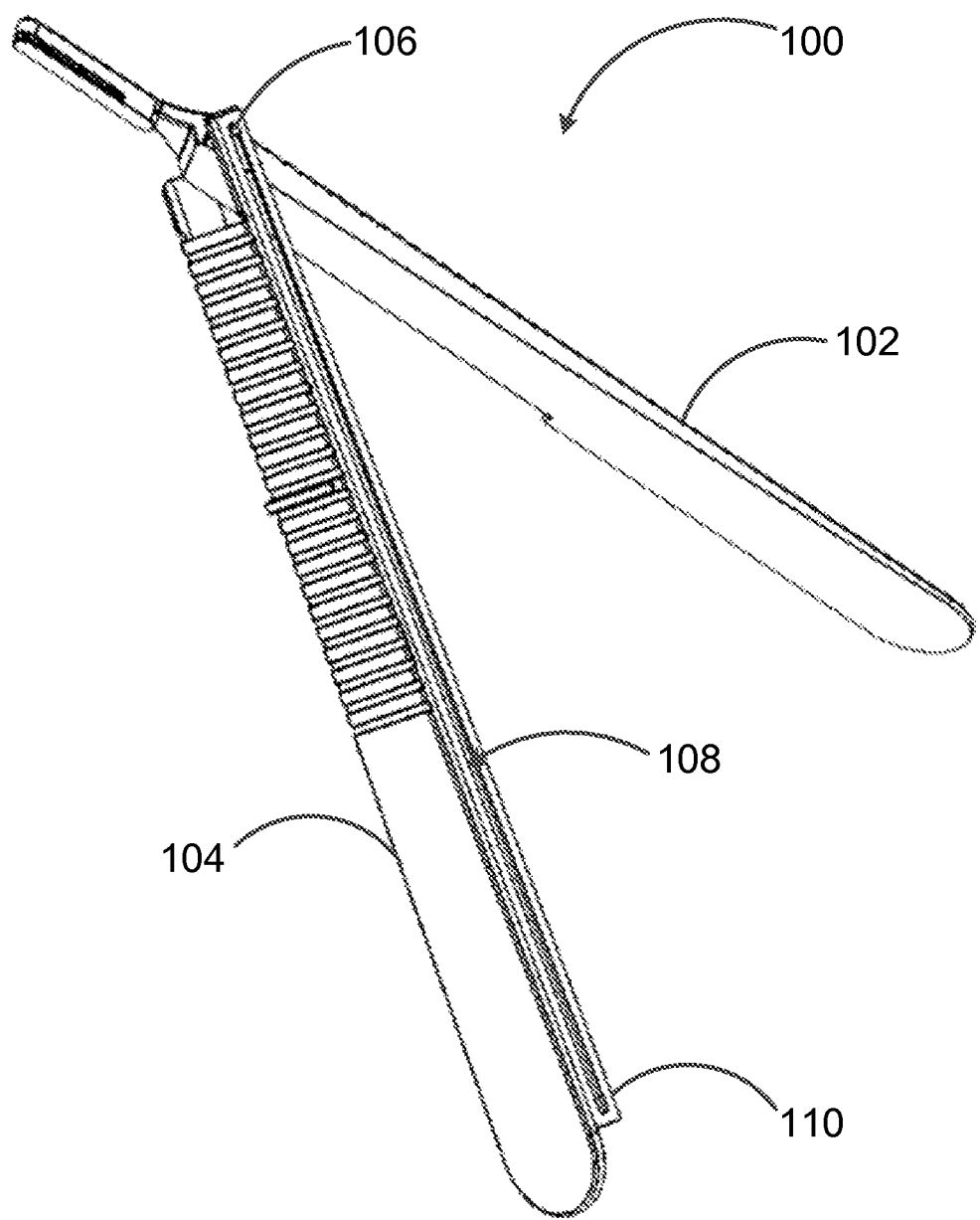
FIG. 11 is a perspective view of a safety scalpel having a pivoting guide channel, according to further embodiments of the present disclosure.

As shown in FIG. 11, further pivoting embodiments of the present disclosure comprise a pair of matched handle halves 102,104 pivotally connected together while allowing the pair of matched handle halves 102,104 to slidingly cooperate between a closed position wherein an engaged blade is exposed and extends outside of the pair of matched handle halves 102,104, and an open position wherein the non-blade bearing handle half 104 is extended relative to the blade-bearing handle half 102 to cover the engaged blade between the pair of matched handle halves 102,104. The non-blade bearing handle half 104 comprises a pair of flanges 110 that project or extend from opposing sides of the non-blade bearing handle half 104. As shown in FIG. 11, the flanges extend along the long-edge of the handle half 104 at opposite sides of the handle. Each of the flanges 110 comprise a guide channel 108 that extends along the length of the flange 110 from the distal end to the proximal end of the non-blade bearing handle half 104. A pair of sliding actuators 106 situated at opposing sides of the distal end of the blade-bearing handle half 102 are each pivotally engaged with a respective guide channel 108 on the non-blade bearing handle half 104 to allow the handle halves 102,104 to pivot relative to each other and separate along the entire length of the handle halves 102,104. Each of the sliding actuators 106 are further in sliding engagement within the respective guide channel 108 on the non-blade bearing handle half 104 to allow sliding translation of the pair of handle halves 102,104 relative to each other. In this way, each sliding actuator 106 slidingly engages with a corresponding guide channel 108 to allow the handle halves 102,104 to both slide and pivot relative to each.

According to certain embodiments, the pair of sliding actuators 106 comprises a pair of bosses situated at opposing sides of the blade-bearing handle half 102. In such embodiments, the pair of bosses are in friction fit with the corresponding guide channel 108 to allow the positioning of the sliding handle halves 102,104 to be fixed in the desired position and permit sliding translation upon application of force. In other embodiments, the safety scalpel 100 can further comprise a locking mechanism for fixing the safety scalpel 100 in the closed position or the open position.

Kits

In use, the safety scalpel may be provided in a sterile condition within a package or container, alone or a component of a kit. Generally the blade may be provided separately and is engaged just before use. However, for some applications, the safety scalpel of the present disclosure may be packaged with a blade already engaged. In some embodiments, the safety scalpel of the present disclosure may be provided for disposable use and packaged with a blade permanently engaged.

With reusable embodiments, once a blade attached to the safety scalpel of the present disclosure has been used or when it needs to be replaced for other reasons, practitioners of medical sciences or other users can remove the blade from the blade slot and discard the blade. The safety scalpel can subsequently have another blade secured to the blade receptacle. Engaging the blade onto the blade receptacle can be performed when the safety scalpel is in the "open position", the "closed position" or somewhere in between.

While particular exemplary embodiments are discussed above as to the size and shape of the safety scalpel of the present disclosure, the size and shape of the safety scalpel is not limited to the structures described. For example, the safety scalpel may not be tapered and may be a uniform width from the distal end to the proximal end. It is contemplated that the scalpel handle size can, without limitation, include the following sizes B3, B3L, 3, 3G, 3L, 3SS, 4, 4G, 4L, 5, 5B, 6, 7, 8, 9, as well as rounded handles. Additionally, the safety scalpel of the present disclosure is not limited by the blade shape or size, and can be used with, for example, blade sizes that conform to ISO 7740.

The disclosures of all patents, patent applications, publications and database entries referenced in this specification are hereby specifically incorporated by reference in their entirety to the same extent as if each such individual patent, patent application, publication and database entry were specifically and individually indicated to be incorporated by reference.

Although the invention has been described with reference to certain specific embodiments, various modifications thereof will be apparent to those skilled in the art without departing from the spirit and scope of the invention. All such The embodiments of the invention in which an exclusive property or privilege is claimed are defined as follows:

1. A safety scalpel comprising:
   a pair of matched handle halves pivotally connected together wherein a first handle half of the pair is provided with a blade receptacle for engaging therewith a blade and a second handle half of the pair is provided with a guard flange, the pair of matched handle halves slidingly cooperative into: (i) a closed position wherein an engaged blade is exposed and extends outside of the pair of matched handle halves, and (ii) an open position wherein the the second handle half is extended relative to the first handle half whereby the engaged blade is covered by the guard flange;
   one or more guide channels extending along the length of one of the pair of handle halves along which the other handle half of the pair slidingly travels; and
   one or more sliding actuators situated on the other handle half and pivotally engaged with a respective one of the guide channels to allow the handle halves to pivot relative to each other, the one or more sliding actuators further in sliding engagement within the respective one of the guide channels to allow sliding translation of the pair of handle halves relative to each other;
   wherein the one or more actuators comprise a pair of sliding actuators situated at opposing sides of a distal end of the first handle half and the one or more guide channels comprise a pair of guide channels extending from a distal end to a proximal end of the second handle half, the pair of guide channels comprising a pair of flanges extending on opposing sides of the second handle half, each guide channel slidingly engaging with a respective one of the sliding actuators to allow the handle halves to slide relative to each other.

2. The safety scalpel of claim 1, further comprising a locking mechanism for fixing the safety scalpel in the closed position or the open position.

3. The safety scalpel of claim 1, wherein the second handle half comprises the sliding actuator and the first handle half comprises the guide channel extending from a distal end to a proximal end of the first handle half, the guide channel at the proximal end further comprising a downwardly extending portion for guiding the distal end of the second handle half in a downward direction away from the first handle half in a pivotally sliding manner.

4. The safety scalpel of claim 3, wherein the sliding actuator comprises a machined-in spring to facilitate engagement with the downwardly extending portion of the guide channel.

5. The safety scalpel of claim 1, wherein the second handle half further comprises an additional guard flange projecting therefrom to further cover the engaged blade when in said open position.

6. The safety scalpel of claim 5, wherein the first handle half comprises a recess corresponding in size with the guard flange, the guard flange is stowable within the recess when the safety scalpel is in said closed position.

7. The safety scalpel of claim 1, wherein the guard flange partially projects from the distal end of the second handle half.

8. The safety scalpel of claim 1, wherein the safety scalpel comprises a sterilizable material.

9. The safety scalpel of claim 1, wherein the safety scalpel is disposable.

10. The safety scalpel of claim 1, wherein the one or more sliding actuators comprise a pair of bosses situated at opposing sides of the first handle half.

11. The safety scalpel of claim 10, wherein the pair of bosses are in friction fit with the pair of guide channels.

12. A safety scalpel comprising:
   a pair of matched handle halves pivotally connected together wherein a first handle half of the pair is provided with a blade receptacle for engaging therewith a blade, the pair of matched handle halves slidingly cooperative into: (i) a closed position wherein an engaged blade is exposed and extends outside of the pair of matched handle halves, and (ii) an open position wherein a second handle half of the pair is extended relative to the first handle half to cover the engaged blade between the pair of matched handle halves;
   a pair of guide channels extending from a distal end to a proximal end of the second handle half, the pair of guide channels comprising a pair of flanges extending on opposing sides of the second handle half;
   a pair of sliding actuators situated at opposing sides of a distal end of the first handle half, each sliding actuator of the pair pivotally engaged with a respective guide channel on the second handle half to allow the handle halves to pivot relative to each other, each of the sliding actuators further in sliding engagement within the respective guide channel on the second handle half to allow sliding translation of the pair of handle halves relative to each other, wherein each sliding actuator slidingly engages with a corresponding one of the guide channels to allow the handle halves to both slide and pivot relative to each other.

13. The safety scalpel of claim 12, wherein the pair of sliding actuators comprises a pair of bosses situated at opposing sides of the first handle half.

14. The safety scalpel of claim 13, wherein the pair of bosses are in friction fit with the corresponding one of the guide channels.

15. The safety scalpel of claim 12, further comprising a locking mechanism for fixing the safety scalpel in the closed position or the open position.

16. The safety scalpel of claim 12, wherein the safety scalpel comprises a sterilizable material.

17. The safety scalpel of claim 12, wherein the safety scalpel is disposable.

* * * * *